United States Patent
Ong

(10) Patent No.: US 8,248,067 B2
(45) Date of Patent: Aug. 21, 2012

(54) APPARATUS AND METHODS FOR ESTIMATING DOWNHOLE FLUID COMPOSITIONS

(75) Inventor: Joo Tim Ong, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 485 days.

(21) Appl. No.: 12/348,068

(22) Filed: Jan. 2, 2009

(65) Prior Publication Data

US 2009/0157315 A1 Jun. 18, 2009

Related U.S. Application Data

(63) Continuation-in-part of application No. 11/233,900, filed on Sep. 23, 2005, now Pat. No. 7,501,819.

(51) Int. Cl.
*G01V 3/00* (2006.01)

(52) U.S. Cl. ......................................................... 324/303

(58) Field of Classification Search ........... 324/300–322
See application file for complete search history.

(56) References Cited

U.S. PATENT DOCUMENTS

| | | | |
|---|---|---|---|
| 4,536,711 A * | 8/1985 | King et al. ..................... | 324/306 |
| 4,785,245 A | 11/1988 | Lew et al. | |
| 4,901,018 A | 2/1990 | Lew | |
| 5,497,087 A | 3/1996 | Vinegar et al. | |
| 5,498,960 A | 3/1996 | Vinegar et al. | |
| 5,684,399 A | 11/1997 | Bayer | |
| 5,936,405 A * | 8/1999 | Prammer et al. ............... | 324/303 |
| 6,046,587 A | 4/2000 | King et al. | |
| 6,081,116 A | 6/2000 | Wu et al. | |
| 6,111,409 A * | 8/2000 | Edwards et al. ............... | 324/303 |
| 6,242,912 B1 | 6/2001 | Prammer et al. | |
| 6,255,819 B1 | 7/2001 | Day et al. | |
| 6,337,568 B1 | 1/2002 | Tutunji et al. | |
| 6,346,813 B1 * | 2/2002 | Kleinberg ....................... | 324/303 |
| 6,512,371 B2 | 1/2003 | Prammer | |
| 6,661,226 B1 | 12/2003 | Hou et al. | |
| 6,737,864 B2 * | 5/2004 | Prammer et al. ............... | 324/303 |
| 6,774,634 B2 * | 8/2004 | Cosman ......................... | 324/321 |
| 6,825,657 B2 * | 11/2004 | Kleinberg et al. ............. | 324/303 |
| 6,972,564 B2 | 12/2005 | Chen et al. | |
| 7,126,332 B2 * | 10/2006 | Blanz et al. .................... | 324/303 |
| 7,176,682 B2 | 2/2007 | Galford et al. | |
| 7,205,762 B2 | 4/2007 | Blanz et al. | |
| 7,298,142 B2 | 11/2007 | Hursan et al. | |
| RE40,167 E * | 3/2008 | Edwards et al. ............... | 324/303 |
| 7,368,909 B2 | 5/2008 | Blanz et al. | |
| 7,388,373 B2 | 6/2008 | Lenormand et al. | |
| 7,501,819 B2 * | 3/2009 | Ong ................................ | 324/306 |

FOREIGN PATENT DOCUMENTS

| | | |
|---|---|---|
| EP | 0496330 A2 | 1/1992 |
| EP | 0691526 A1 | 1/1996 |
| WO | 9859220 A2 | 12/1998 |
| WO | 0136919 A1 | 5/2001 |

* cited by examiner

*Primary Examiner* — Dixomara Vargas
(74) *Attorney, Agent, or Firm* — Cantor Colburn LLP

(57) ABSTRACT

An apparatus and method for estimating a property of a species of the hydrocarbon in a downhole fluid are provided. In one aspect, the method may include: imparting a magnetic field on the fluid to align nuclei of the fluid with a direction of the primary magnetic field; imparting a perturbing radio frequency signal on the fluid to excite the nuclei of the fluid; detecting a radio frequency signal emitted by the excited nuclei of the fluid; estimating a frequency shift between the perturbing radio frequency and the detected radio frequency; and estimating using the frequency shift a property of one or more species of the hydrocarbons in the fluid.

18 Claims, 16 Drawing Sheets

US 8,248,067 B2

APPARATUS AND METHODS FOR ESTIMATING DOWNHOLE FLUID COMPOSITIONS

CROSS-REFERENCE TO RELATED APPLICATION

This application is a continuation-in-part of U.S. Ser. No. 11/233,900 filed Sep. 23, 2005, which claims priority from United Kingdom Patent Application No. 0421266.8, filed on 24 Sep. 24, 2004, all of which are hereby incorporated by reference in their entirety.

BACKGROUND

The present disclosure relates generally to a measurement apparatus and methods for estimating downhole fluid characteristics.

In the oil and gas industry it has become increasingly important in recent years to obtain measurements of the flow rate and phase ratio of multiphase fluids such as those produced by drilling operations and the compositions of the downhole fluid.

In order to measure the flow rate and ratio properties of such multiphase fluids accurately enough to satisfy the operator's requirements it is currently known to use techniques such as Nuclear Magnetic Measurement (NMR) and Electronic Spin Resonance (ESR) analysis. However, currently available systems for measuring such properties using these techniques require a number of separate components which employ a variety of operational and analytical techniques and often involve a number of discrete devices each adapted to measure a particular property of the fluid flow. For example a device for detecting the fraction of one phase may be supplied along with a device for detecting the fraction of another phase and another device to measure the overall flow rate. Also, such techniques are generally not utilized for compositional analysis of hydrocarbons in downhole fluids.

SUMMARY

In one aspect, a method analyzing composition of a hydrocarbon in a downhole fluid is provided, which may include: imparting a magnetic field on the fluid to align nuclei of the fluid with a direction of the primary magnetic field; imparting a perturbing radio frequency signal on the fluid to excite the nuclei of the fluid; detecting a radio frequency signal emitted by the excited nuclei of the fluid; estimating a frequency shift between the imparted radio frequency signal and the detected radio frequency signal; and estimating a composition of the hydrocarbon using the frequency shift.

In another aspect, an apparatus according to one embodiment of the disclosure may include: a magnet configured to impart a magnetic field in a region of the downhole fluid to align nuclei of the fluid along a particular direction; a transmitter configured to impart a radio frequency signal in the region of the downhole fluid; a receiver configured to receive a radio frequency signal from the fluid responsive to the imparted radio frequency signal; and a processor configured to estimate a composition of a hydrocarbon in the downhole fluid from a frequency shift between the frequency of the imparted radio frequency signal and the detected radio frequency signal.

Examples of the more important features of the methods and apparatus for analyzing the composition of a hydrocarbon have been summarized rather broadly in order that the detailed description thereof that follows may be better understood and in order that the contributions they represent to the art may be appreciated. There are, of course, additional features of the methods and apparatus that are described hereinafter and which will form the subject of any claims that may be made pursuant to this disclosure.

BRIEF DESCRIPTION OF THE DRAWINGS

For detailed understanding of the apparatus and methods for compositional analysis of hydrocarbons in a downhole fluid, reference should be made to the following detailed description, taken in conjunction with the accompanying drawing, in which like elements are generally designated by like numerals, and in which.

DETAILED DESCRIPTION OF THE DISCLOSURE

Figure 1:
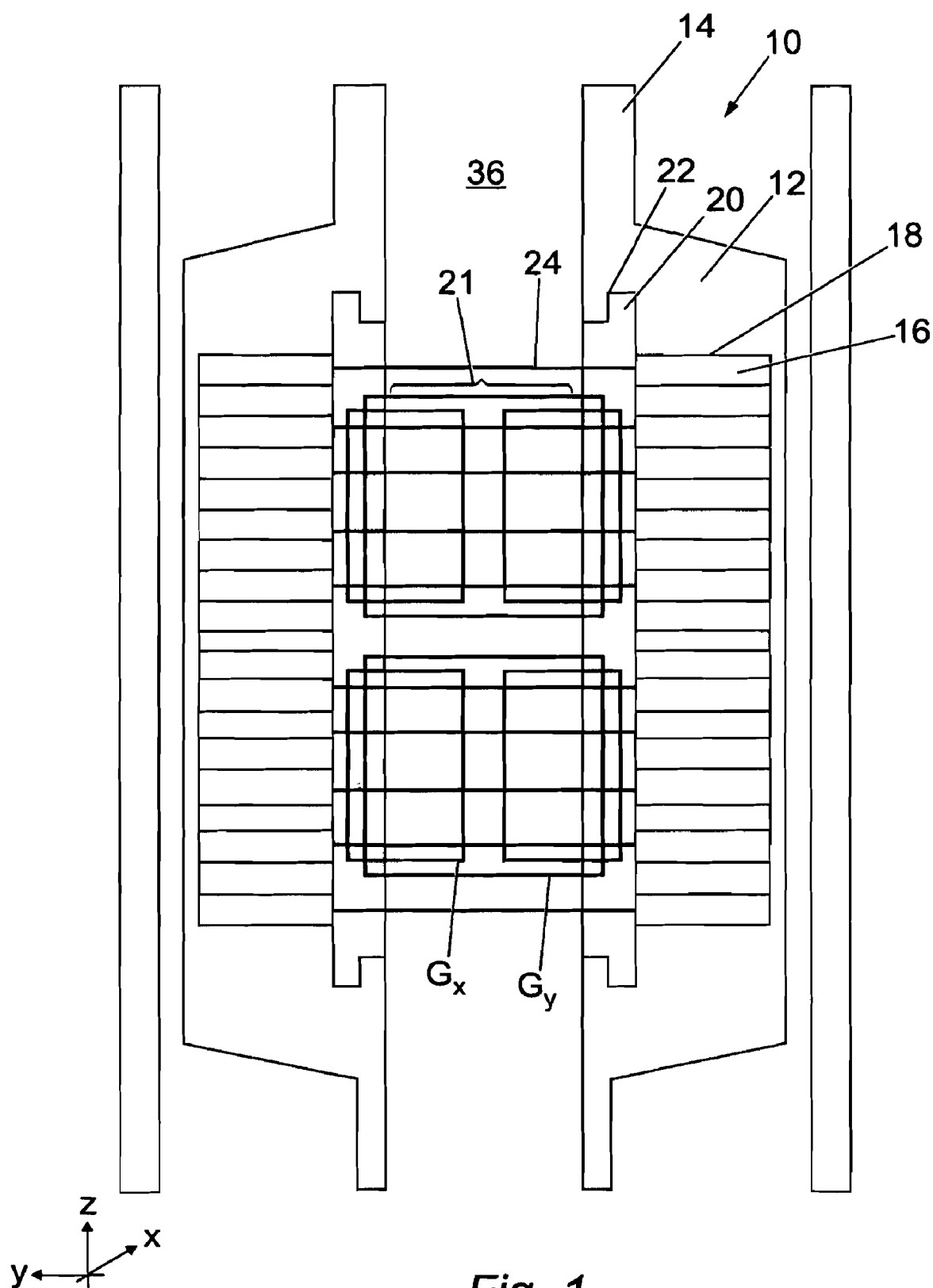
FIG. 1 is a transverse side view of one embodiment of the apparatus according to the present disclosure.
Figure 1A:
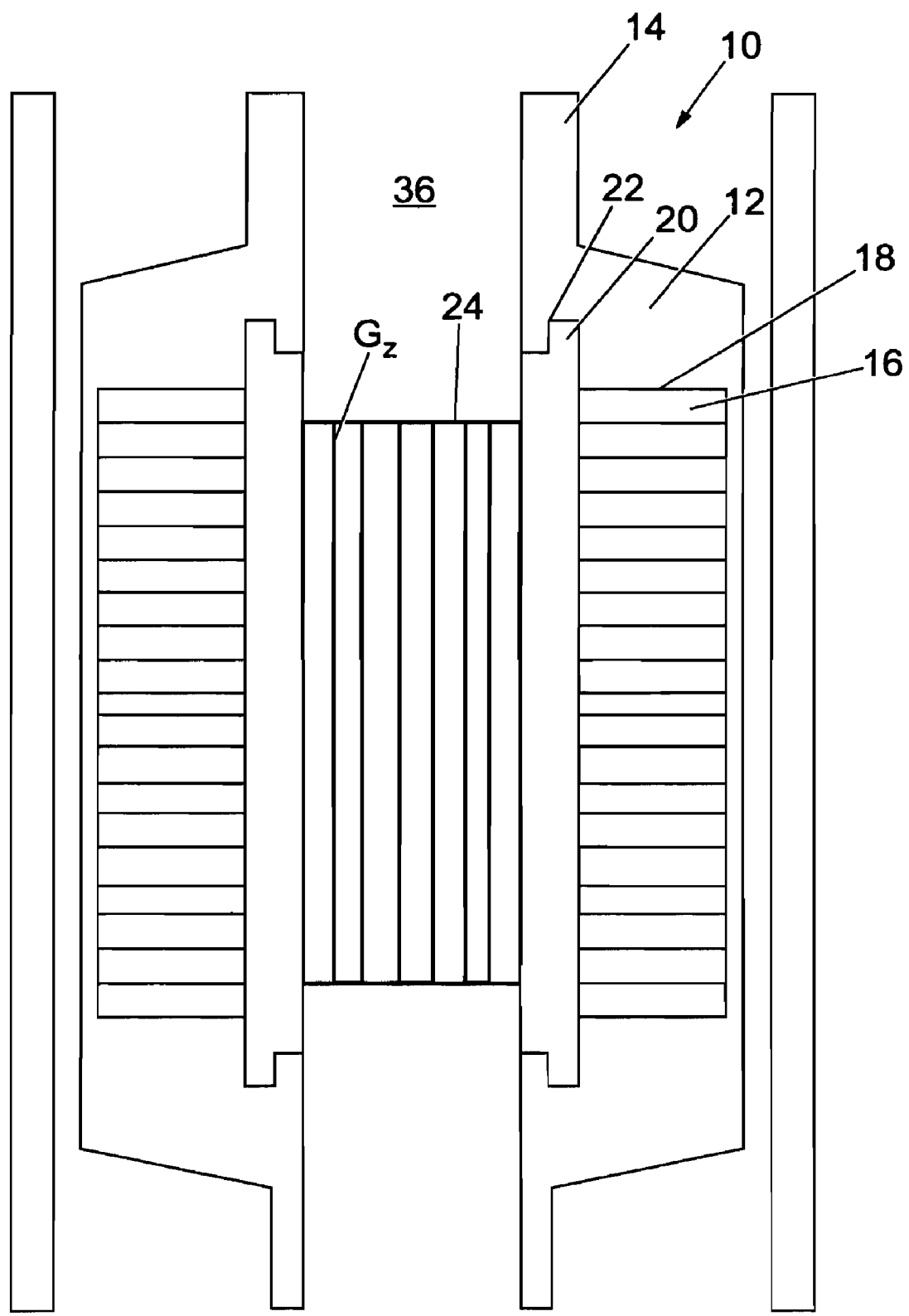
FIG. 1a is a transverse side view of the apparatus of FIG. 1 showing magnetic gradient coils which act in the direction of the z-axis with respect to the reference axes indicated on FIG. 1.
Figure 2:
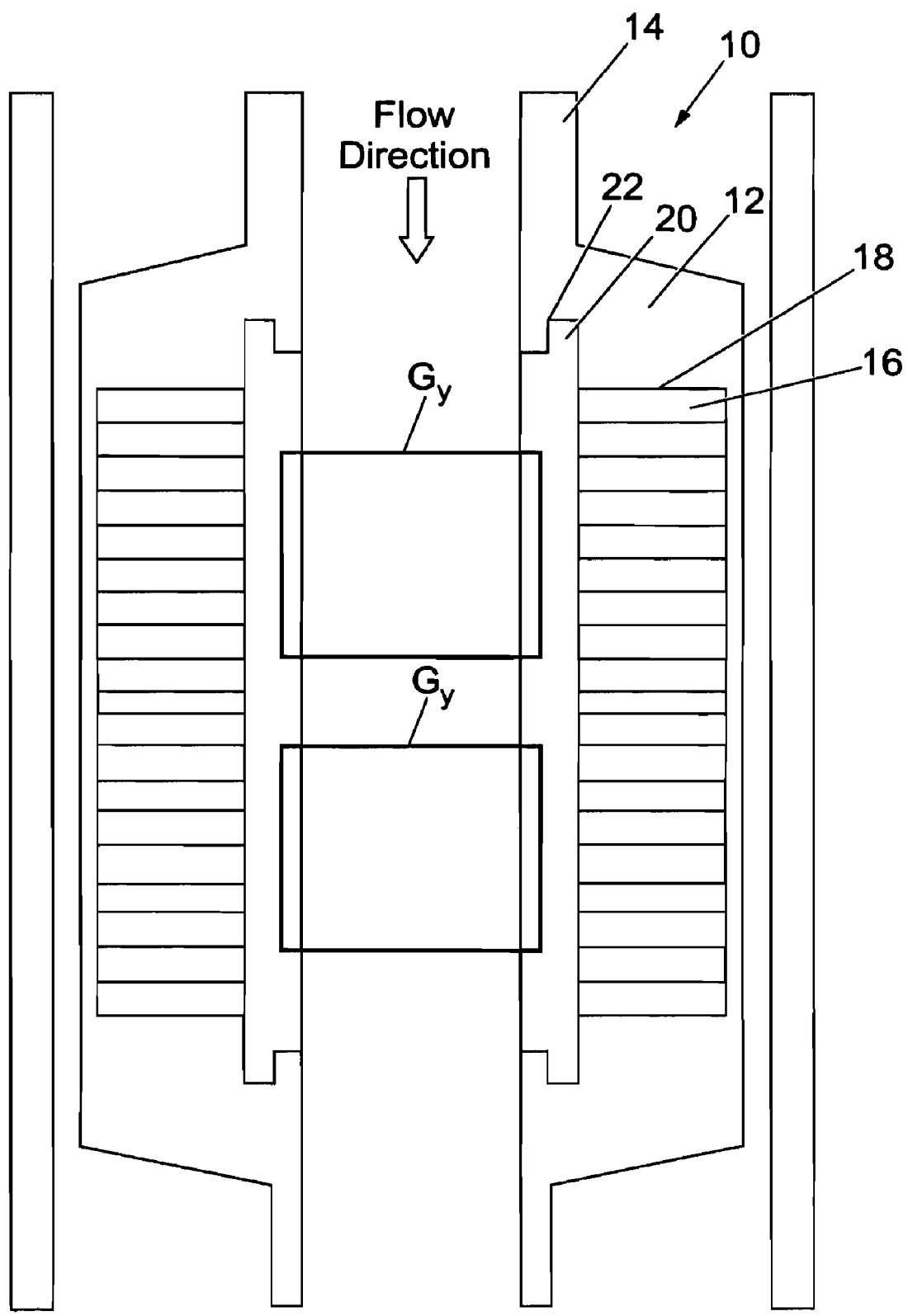
FIG. 2 is a transverse side view of the apparatus of FIG. 1 showing magnetic gradient coils which act in the direction of the y-axis with respect to the reference axes indicated on FIG. 1.
Figure 3:
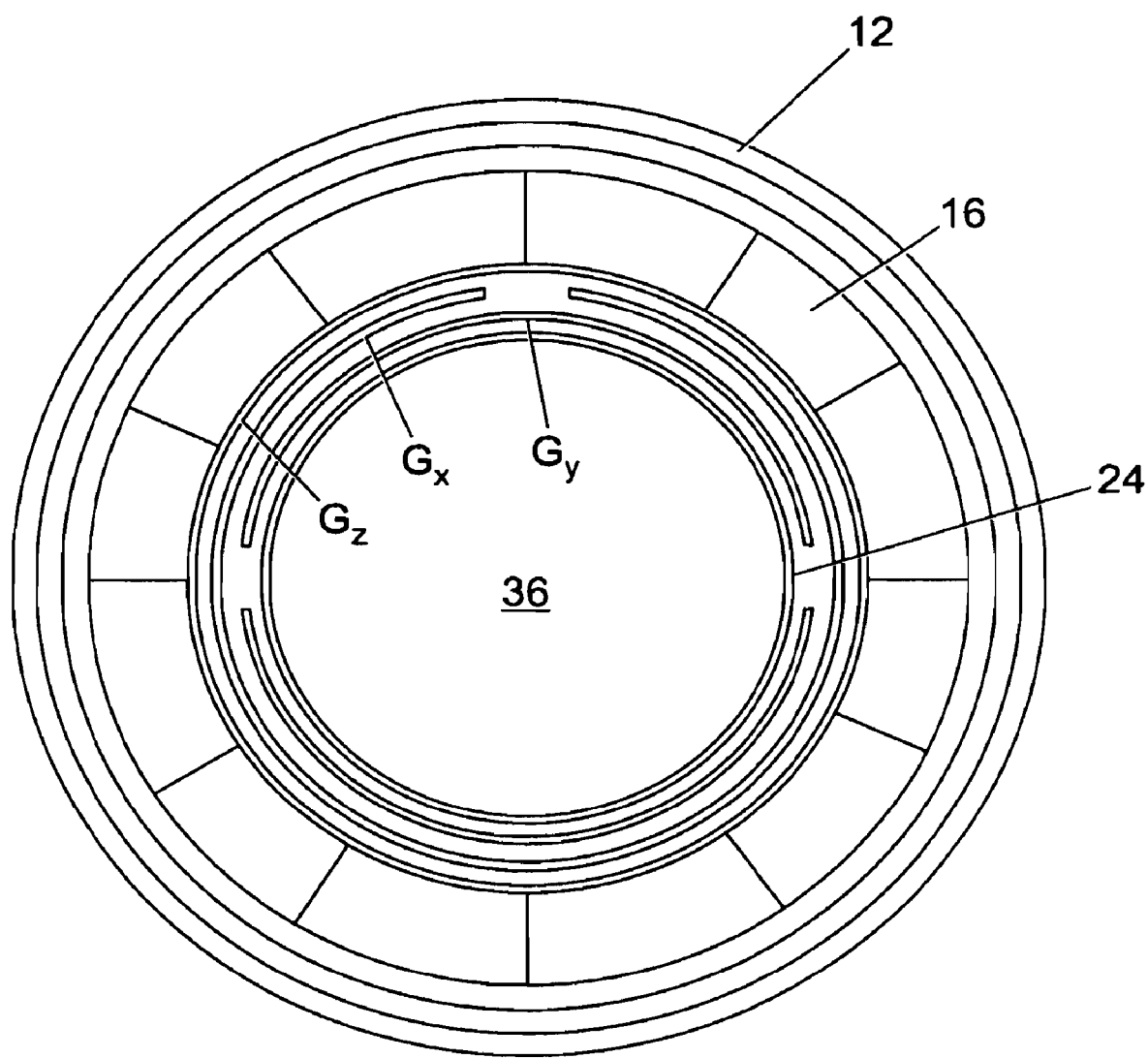
FIG. 3 is a cross sectional view of the apparatus of FIG. 1 showing the components of the magnetic gradient coils which act in the x, y and z directions with respect to the reference axes indicated on FIG. 1.
Figure 4:
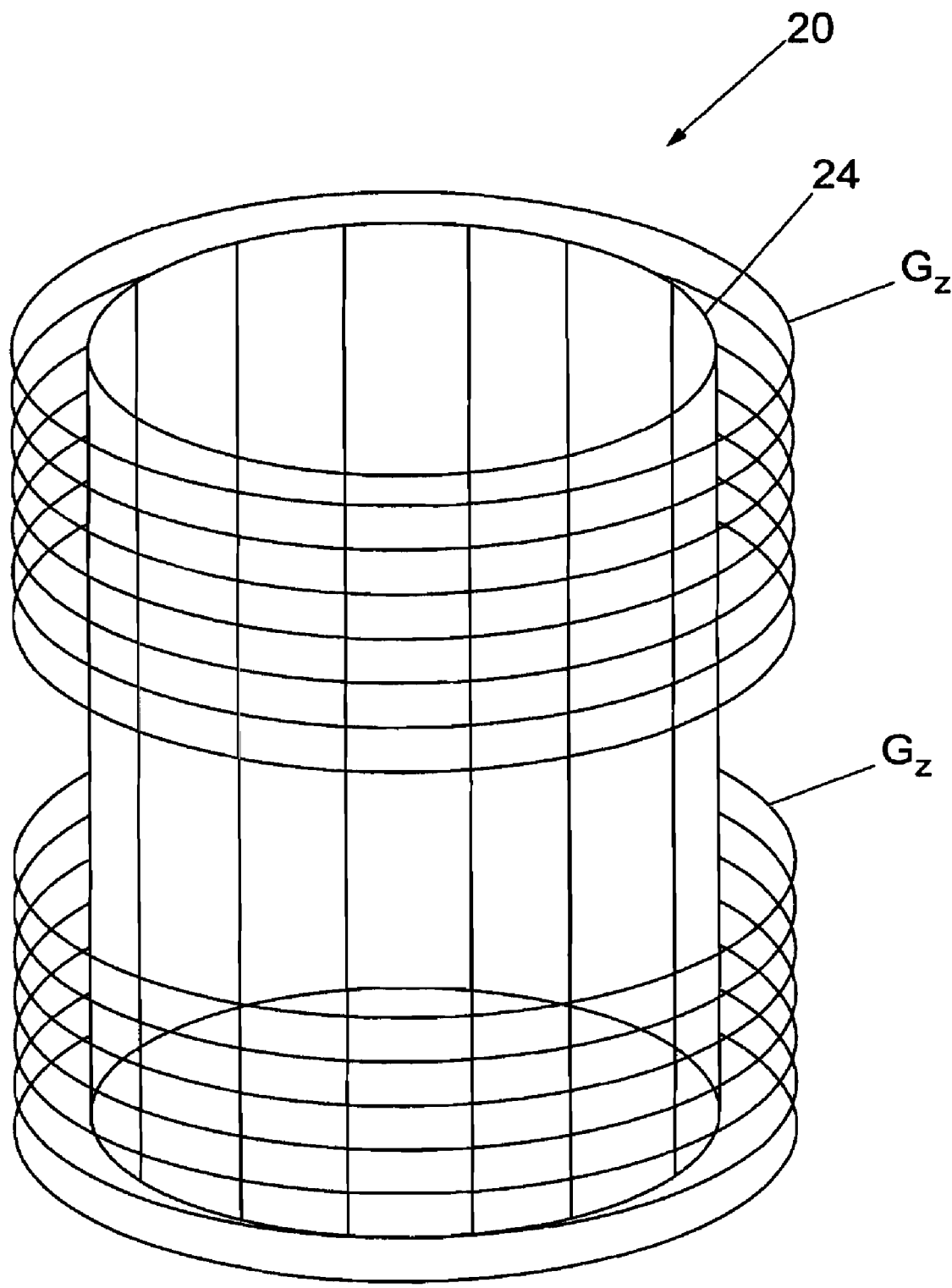
FIG. 4 is a schematic view of the component of the gradient coils which act in the z-axis direction with respect to the reference axes of FIG. 1, arranged around combined transmission and reception coils in accordance with a particular embodiment of the disclosure.
Figure 5:
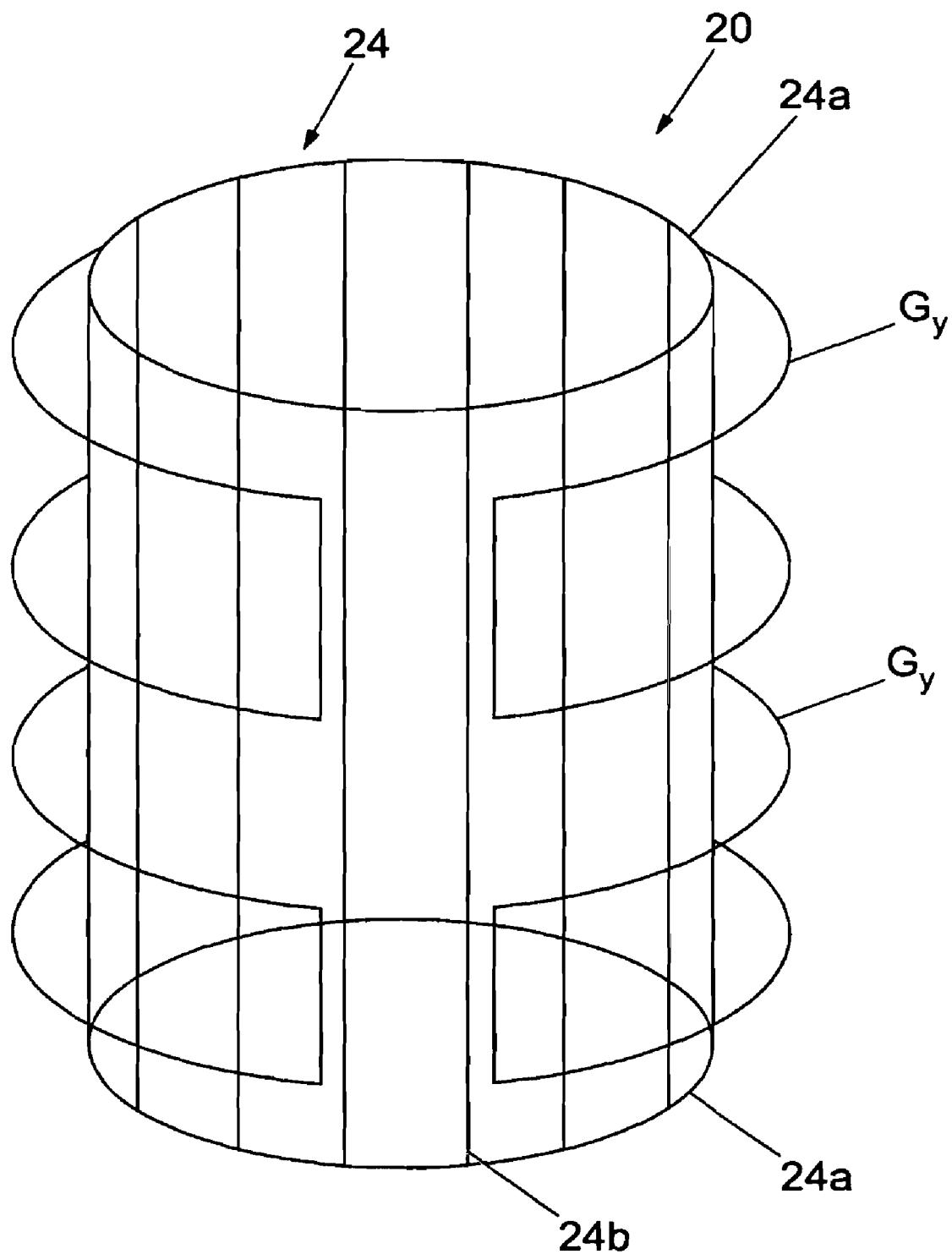
FIG. 5 is a schematic view of the gradient coils which act in the y-axis direction with respect to the reference axes of FIG. 1, arranged around combined transmission and reception coils in accordance with one embodiment of the present disclosure.

Referring to FIG. 1 the apparatus 10 in accordance with the first embodiment of the present invention comprises an outer housing 12 which surrounds a section of a fluid flow pipe 14, such as production tubing, by locking thereto via a suitable locking mechanism. Inside the housing 12 is located a primary permanent magnet 16 in an outermost recess 18 and a secondary electromagnet housing 20 located in an innermost recess 22. The electromagnet housing 20 has located within it an electromagnet 21 which comprises electromagnet coils Gx, Gy and (as shown in FIG. 1a) Gz. Combined transmission and reception coils 24 are also provided within the inner diameter of the electromagnet housing 20.

Outer housing 12 provides magnetic shielding which substantially minimizes leakage of magnetic field outside the apparatus 10, and provides safe handling of the tool. This also improves the signal transmission and reception performance of the coils 24 by minimizing interference from surrounding radio signals such as FM radio signals. Housing 12, in the present embodiment, comprises low permeability iron, (typically $\mu r<1.00$) which provides the main outer body of the apparatus. The material is typically around 10 mm thick around the mid portion of the apparatus 10 and thicker toward the ends of the apparatus 10, typically up to a thickness of around 60 mm. The skilled reader will realize that different thickness and material may be used in the housing 12 in order to suit the particular application.

Figure 6:
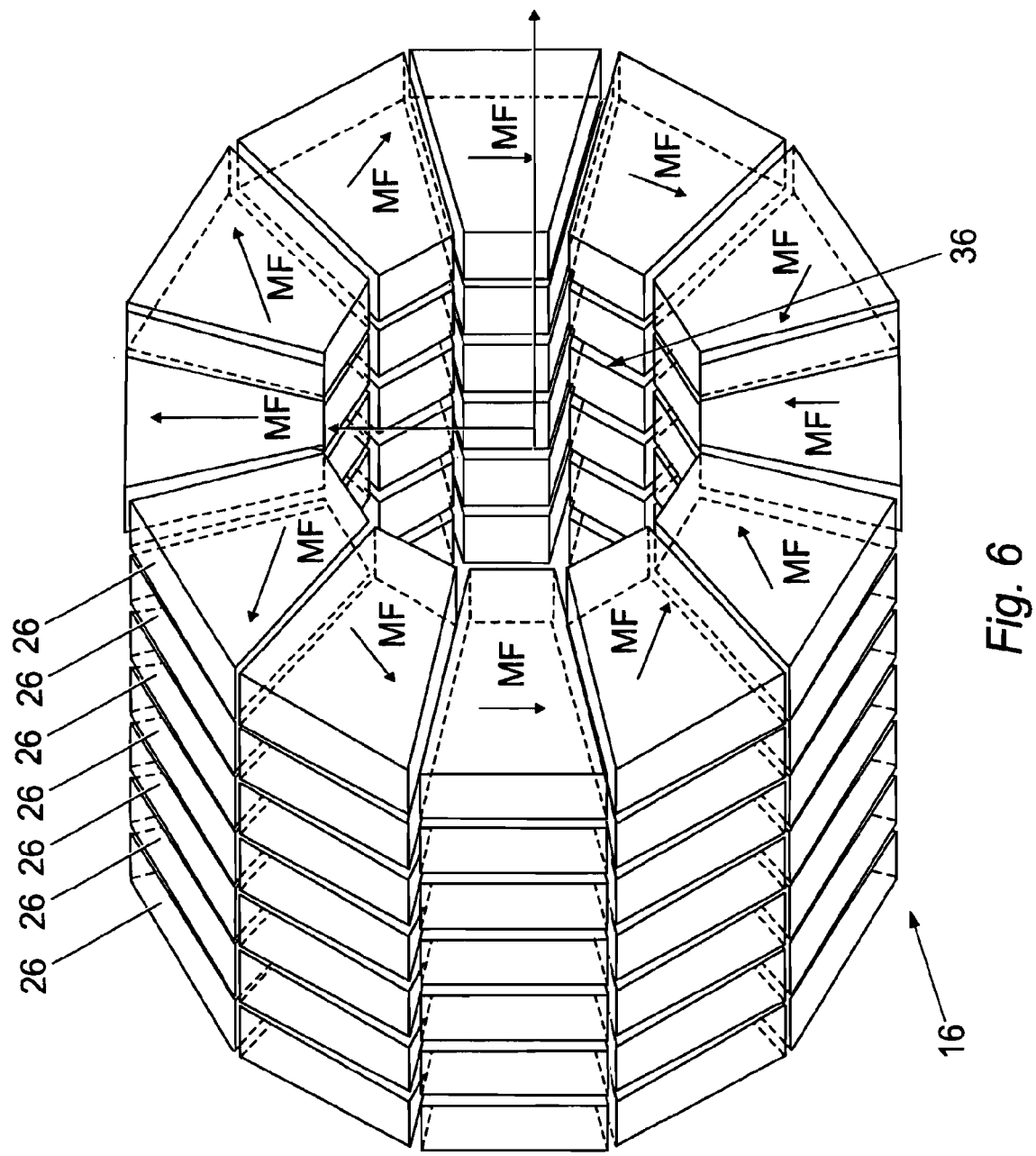
FIG. 6 is an illustration of a magnetic field orientation in order to produce the homogeneous magnet used in accordance with the present disclosure.
Figure 8:
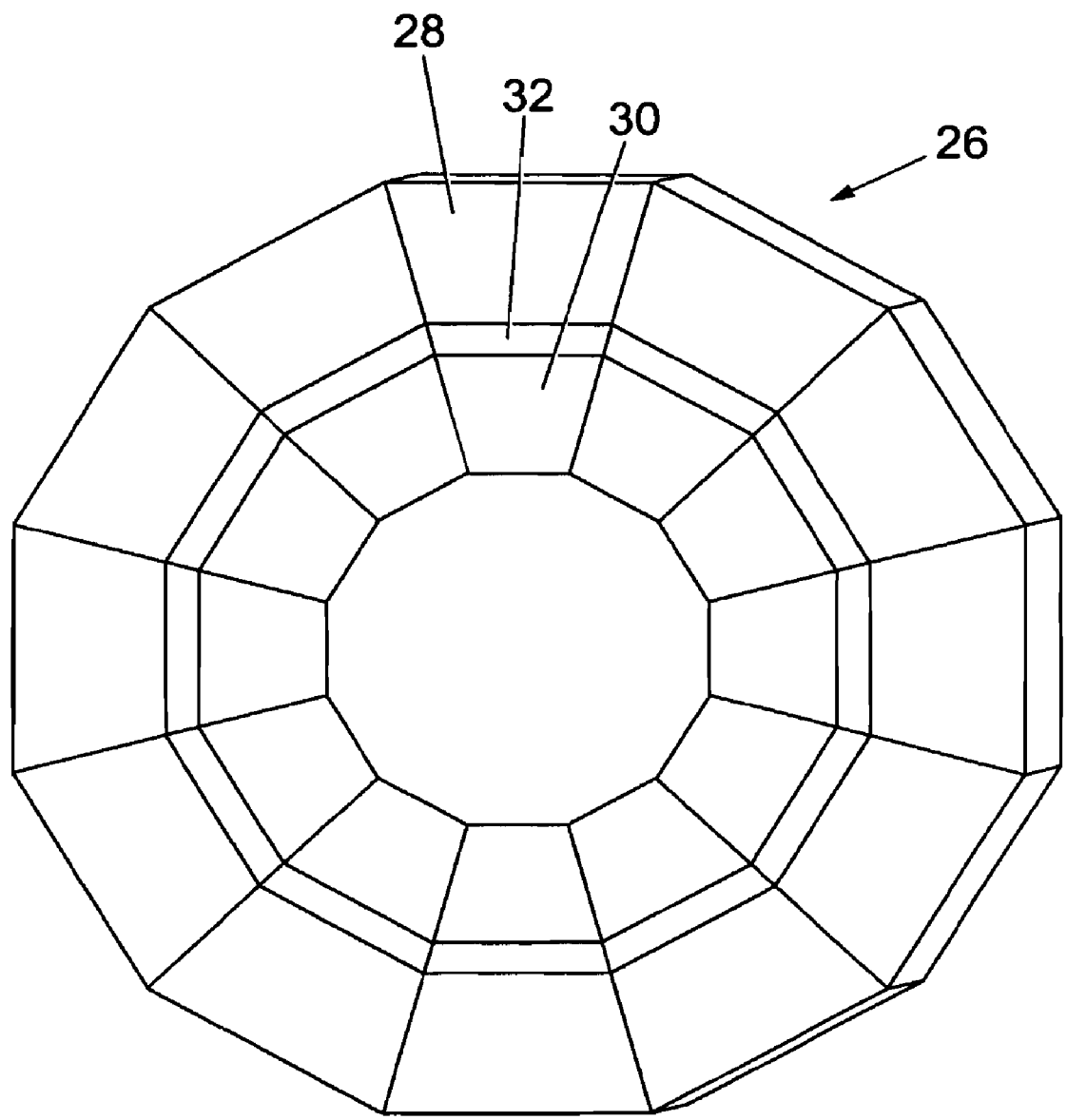
FIG. 8 is a schematic cross sectional diagram of the primary magnet composition used in accordance with the present disclosure.
Figure 9:
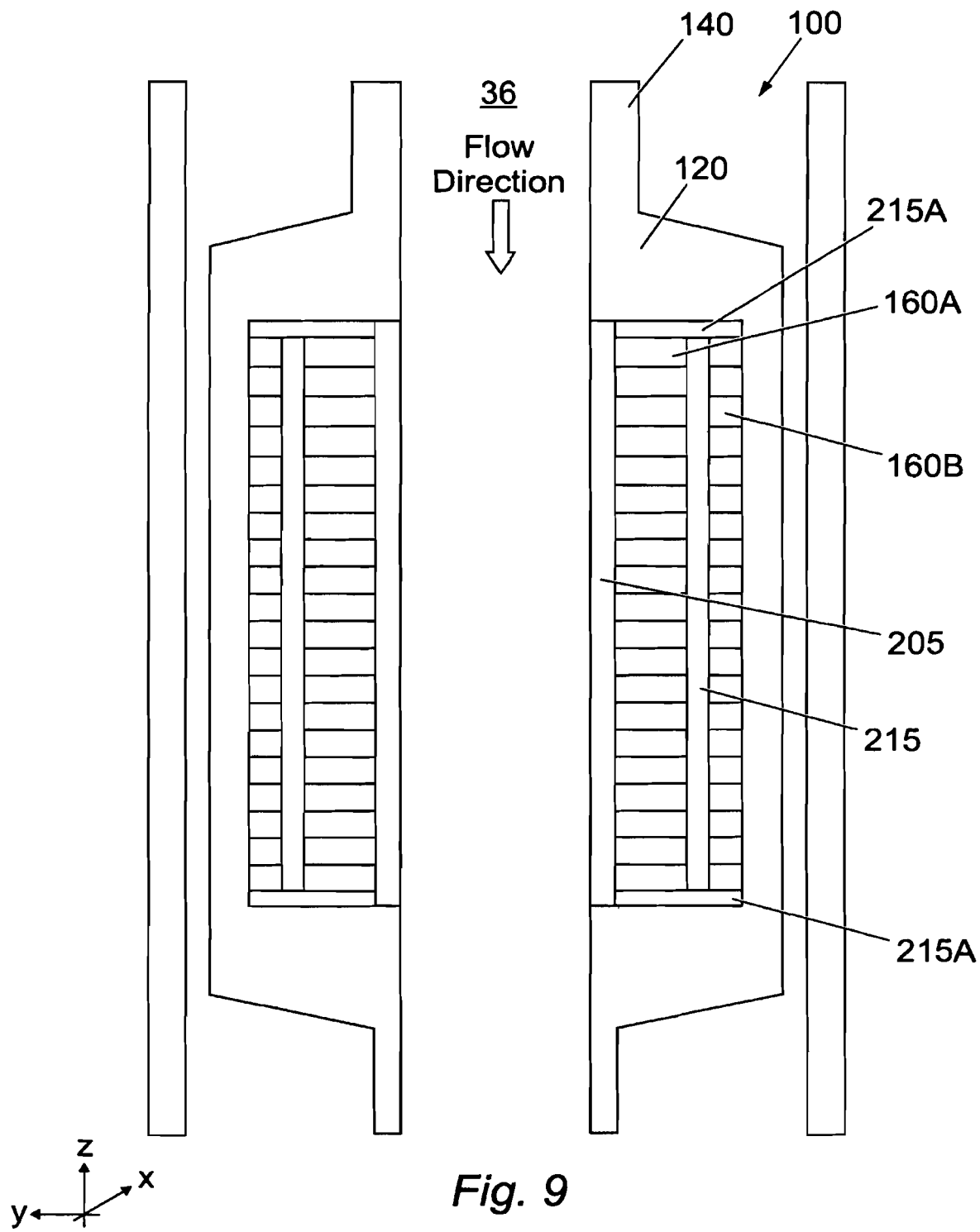
FIG. 9 is a transverse side view of another embodiment of the apparatus according to the present invention without the gradient and transmission coils shown.

Referring particularly to FIGS. 6 and 8, the primary permanent magnet 16 comprises a number of concentrically arranged magnetic cells 26 which are stacked together. Each magnetic cell 26 comprises a number of outer segments 28 (FIG. 8) arranged adjacent a number of inner segments 30 such that a circumferential band of inner segments 30 are arranged within a circumferential band of outer segments 28. Flat plates 32 are positioned between the circumferential band of outer segments 28 and the circumferential band of inner segments 30 such that a circumferential band of plates 32 is located between the outer segments 28 and the inner segments 30. The plates 32 are typically formed of an iron based material having a permeability of greater than 1000.

Aperture 34 is provided in the centre of each cell 26 to allow the flow of fluid therethrough as will be discussed subsequently. When the cells 28 are stacked together they form a throughbore 36 (as shown in FIG. 6) along the length of the magnet 16. The iron plates 32 ensure that the resultant magnetic field produced by inner segments 30 and outer segments 28 is focused toward the center of the aperture 34 of each cell and hence along the throughbore 36 of the apparatus 10.

The skilled reader will understand that the term permanent magnet in this context is taken to mean a magnet which provides a constant magnetic field without requiring, for example, an electric current in order to create the magnetic field. In an alternative embodiment, the permanent magnet may be an electromagnet which provides a continuous and substantially homogeneous magnetic field.

The direction of the magnetic field vectors (indicated by MF in FIG. 6) of each outer 28 and inner 30 segment is carefully arranged during manufacture in order to create a resultant magnetic field for the magnet 16 which is as close to being homogeneous as possible throughout the throughbore of the magnet 16. This ensures that the magnetic field present within the throughbore 36 of the magnet 16 remains consistent within the throughbore 36 irrespective of the location within the throughbore 36 that the magnetic field is experienced. Typically, the required homogeneity is in the region of around 1.0 ppm. This ensures accurate measurements are possible using the apparatus 10 in conjunction with the NMR techniques as will be discussed subsequently.

The secondary electromagnet housing 20 is provided with a combined transmission and reception coil 24 which is capable of both transmitting a radio frequency pulse and detecting the radio frequency emitted by nuclei excited by such a radio frequency pulse. In the embodiment shown in the Figures, the coil 24 comprises a pair of circular loops 24a at the top and bottom of the coil 24 connected by circumferentially spaced connecting coils 24b to form a "birdcage" configuration. This provides the apparatus 10 with the ability to both transmit a radio frequency pulse evenly throughout the throughbore 36 and competently detect radio frequency signals emitted by nuclei at any location within the throughbore 36 of the apparatus 10. Rather than a "birdcage" configuration the coils may alternatively be arranged to provide a "saddle coil" configuration depending upon the application.

Figure 7A:
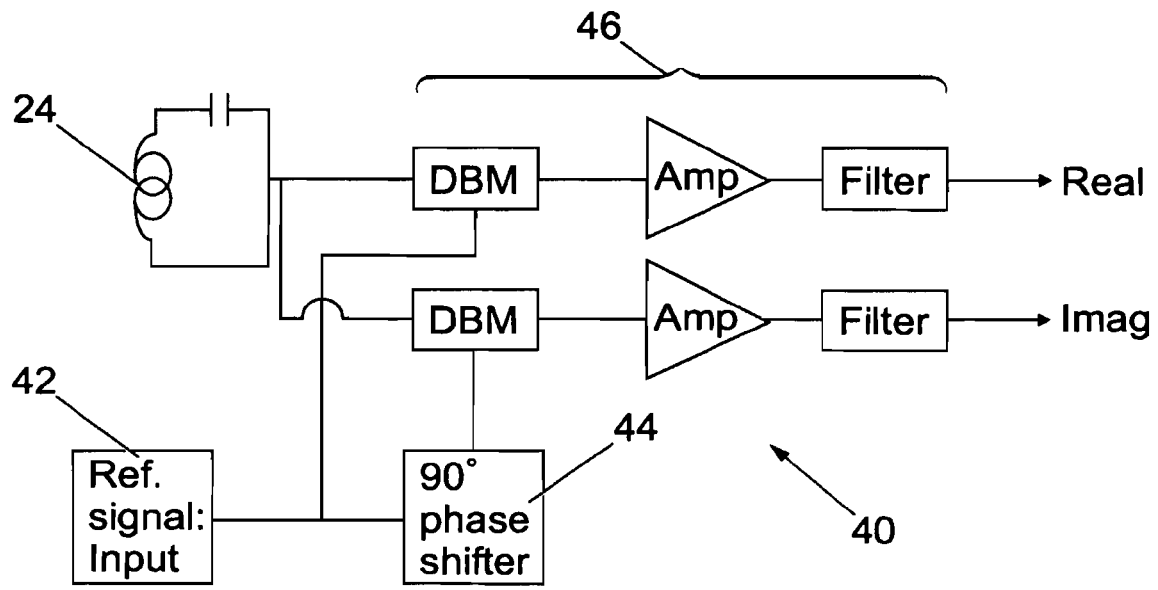
FIG. 7a is a schematic circuit diagram showing the interaction between the various components of the receiving circuit of the combined receiving and transmission coils.
Figure 7B:
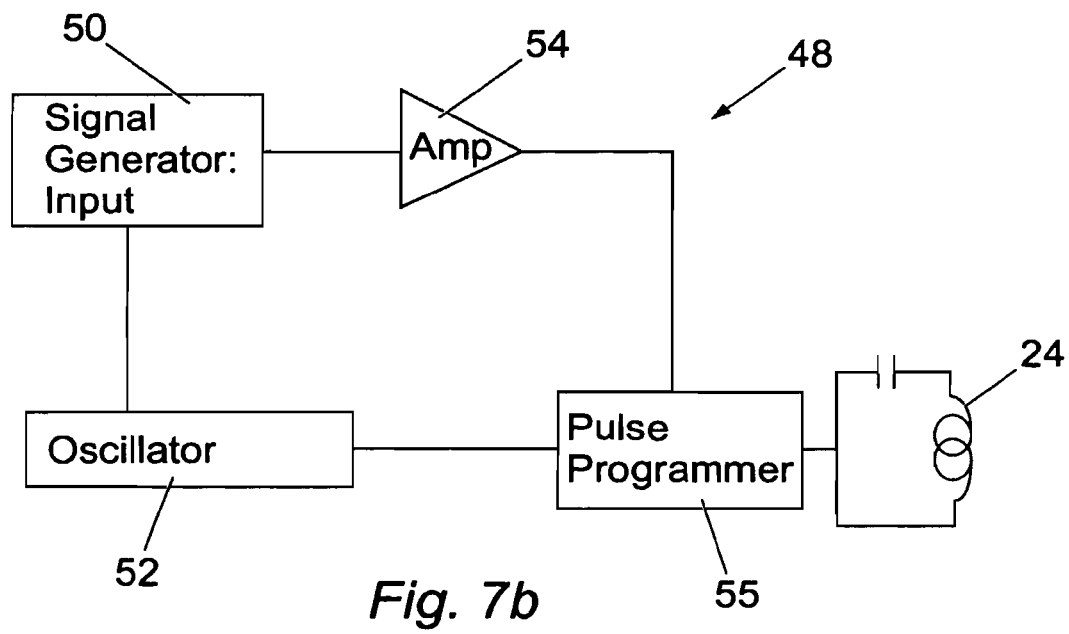
FIG. 7b is a schematic circuit diagram showing the interaction between the various components of the transmitting circuit of the combined receiving and transmission coils.

Referring to FIG. 7a, the receiver circuit 40 of the combined transmission and reception coils 24 comprises a reference signal input generator 42 and a 90° phase shifter 44 connected to a standard amplification and filtering system 46 in order to provide a real and imaginary output signal as a result of the signal received from the coil 24. Referring to FIG. 7b, the transmitter circuit 48 of the combined transmission and reception coils 24 comprises a signal generator input module 50 and an oscillator 52 which are linked to an amp 54 and a pulse programmer 56 in order to transmit the required radio frequency through coil 24. Though illustrated separately in FIGS. 7a and 7b, it will be understood that these circuits may be combined or integrated in order to provide the required transmission and reception capability of combined transmission and reception coils 24.

The secondary electromagnet housing 20 provides the magnetic gradient using coils Gx, Gy, and Gz which selectively (depending upon whether the electromagnet is on or off) provide a graduated magnetic field within the throughbore 36 of the apparatus in the x, y, and z directions respectively indicated by the reference axes R in FIG. 1. This arrangement provides the graduated magnetic field required by the flow rate calculation process described subsequently.

The profile of both the primary permanent magnet 16 and the secondary electromagnet 20 are arranged in the present embodiment, such that they can be housed within the outermost recess 18 and innermost recess 22 respectively in order to maintain a consistent diameter of throughbore 36 through the apparatus 10 such that disturbance of the fluid flowing from the pipe 14 through the apparatus 10 is minimized.

A second embodiment of the present invention having a number of modifications will now be described. Many components of the second embodiment are the same as those described in relation to the first embodiment. Such components will not be described any further. In addition, a number of components in the second embodiment correspond to similar components previously described in relation to the first embodiment, and where this applies, similar reference numerals will be used.

Referring to FIGS. 9 to 13, the apparatus 100 in accordance with the second embodiment of the present invention comprises an outer housing 120 surrounding a primary magnet 160. Primary magnet 160 has an inner ring 160A and an outer ring 160B. A secondary electromagnet is provided in housing 215 as discussed subsequently. Transmission/reception coil housing 205 is provided on the internal bore of the apparatus 100. The housing 205 may be made of a material such as Poly-Ether-Ether-Ketone (PEEK) or a nickel alloy such as Inconel®. The required pressure rating using (PEEK) is generally achieved using a housing 205 having a very thick wall (in the region of 20 mm). Such a wall generally degrades the magnetic field strength at the center of the flow path since magnet strength decreases with radial distance from the magnet. The thickness required using Inconel® is much less (in the region of 7 mm). In addition, the use of Inconel® (which has permeability comparable with free space ($\mu r \approx 1$)), concentrates the magnetic field into the flow path, thereby increasing the magnetic strength homogeneity.

The housing 205 in the present embodiment is provided with recessed tracks (not shown) which are machined onto the outer surface of the housing 205 during manufacture. Additional shapes may also be machined onto the outer surface in order to accommodate components such as the transmission and reception coil capacitors used in the transmission and reception circuit. Electrical insulation (not shown) such as adhesive insulant is also provided between the transmission/reception coil and the housing 205.

Figure 10:
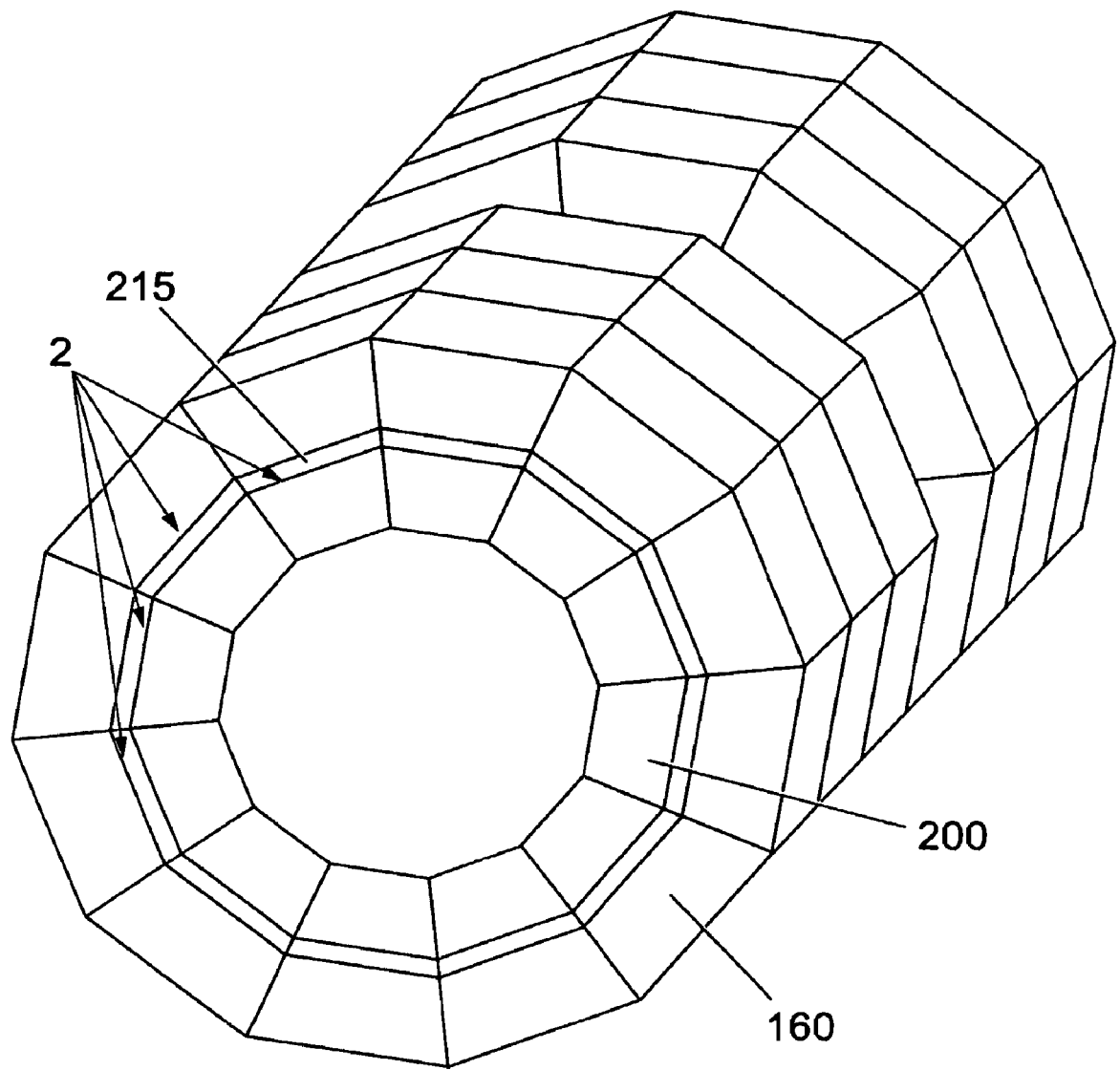
FIG. 10 is a schematic perspective view of the magnet configuration used in the apparatus of FIG. 9.
Figure 11:
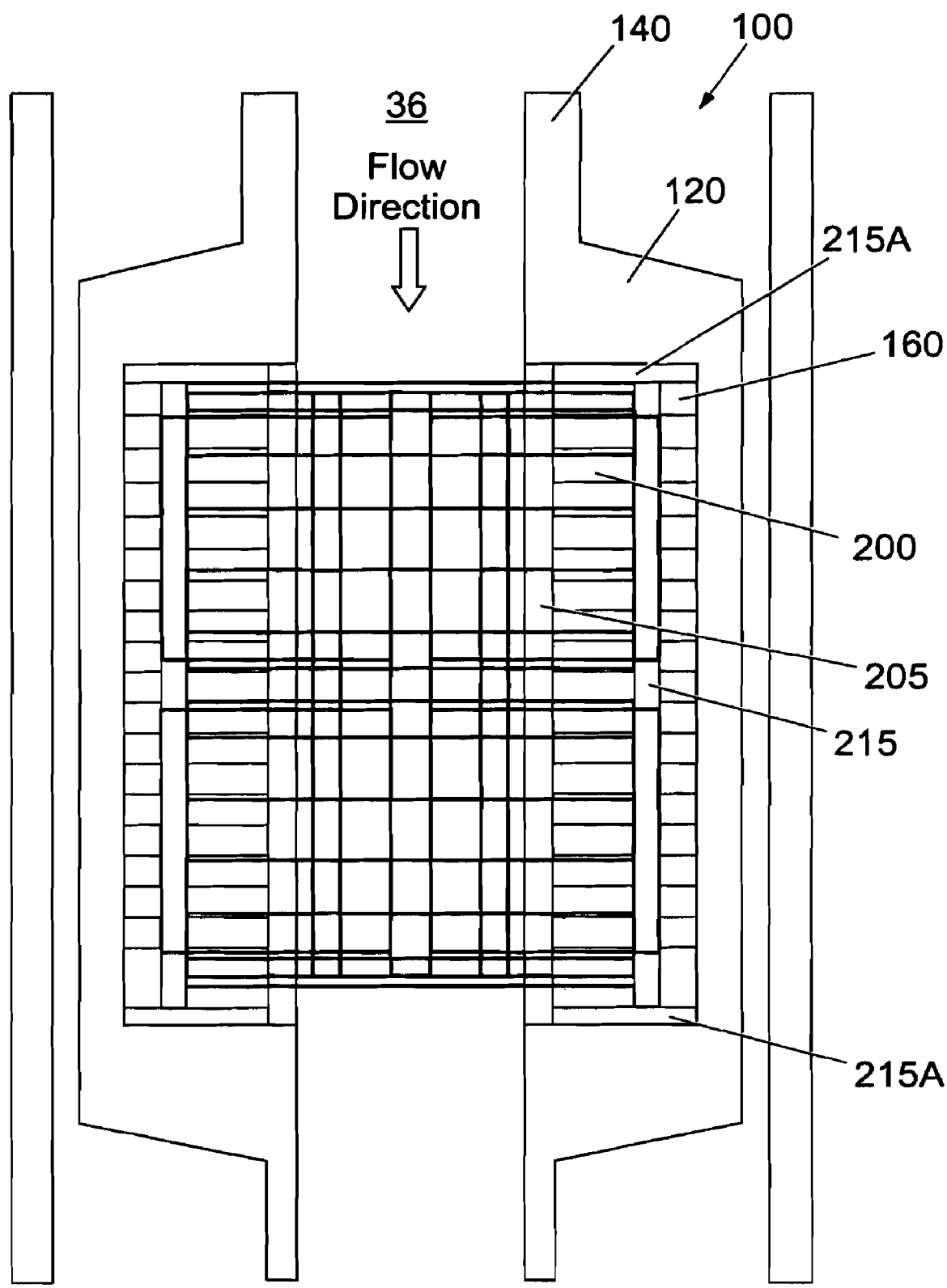
FIG. 11 is a transverse side view of the apparatus of FIG. 9 showing the gradient and transmission coils.

In further contrast, with the first embodiment, the apparatus 100 has gradient coils Gx, Gy, Gz mounted in tubing 215 between the primary magnet portions 160A and 160B. This separates the magnets 160A and 160B from one another which increases the combined efficiency of the magnets in producing a high strength homogeneous magnetic field in the flow path. The tubing 215 also provides mechanical support to retain the primary magnet and to provide support against the pressure exerted from the flow. In the present embodiment, the tubing 215 is made from high permeability iron and is dodecagonal in shape (as shown in FIG. 10). A pair of axial end members 215A are also provided in order to provide a magnetically permeable path for the magnetic field.

Figure 12:
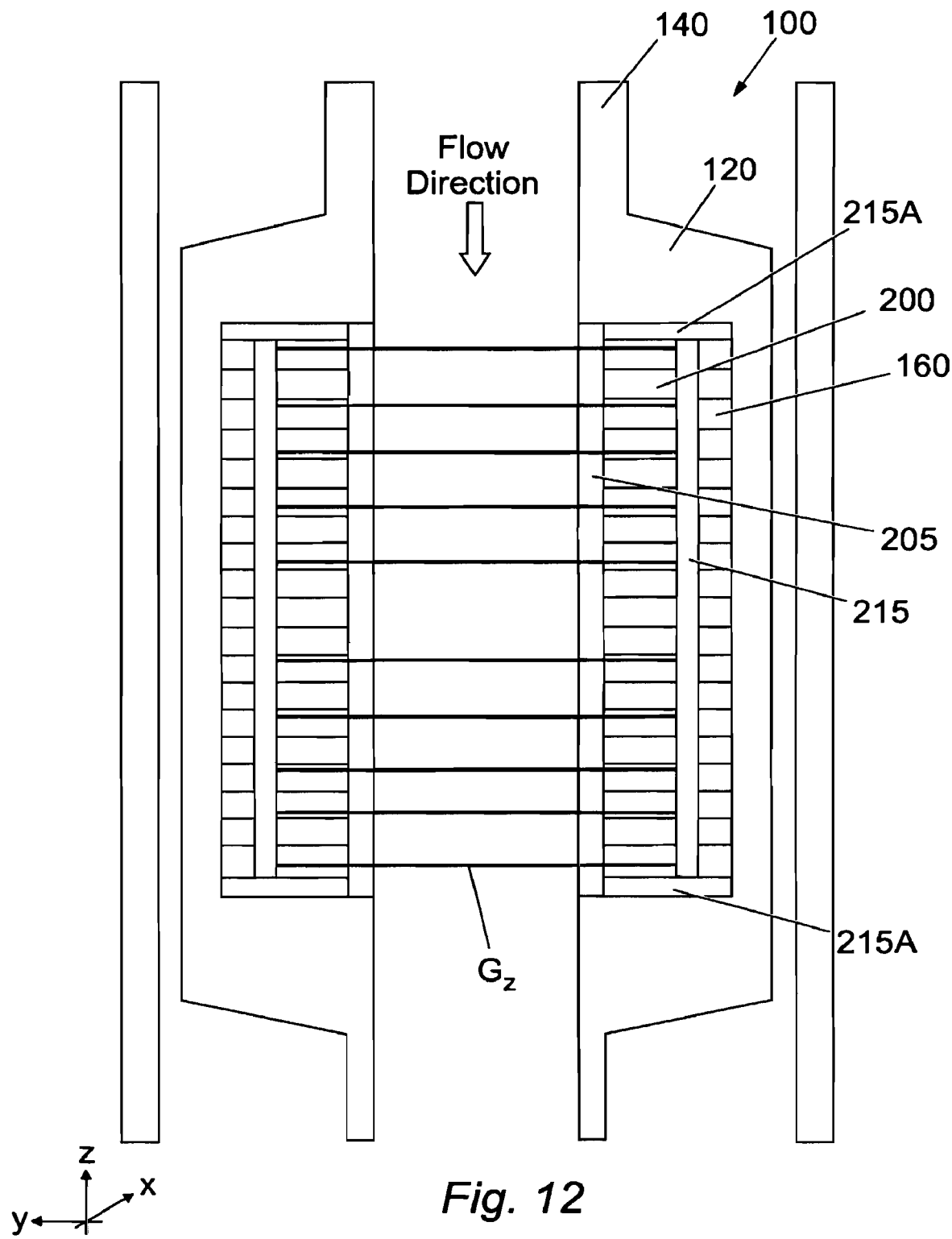
FIG. 12 is a schematic view of the component of the gradient coils of FIG. 10 which act in the z-axis direction.
Figure 13:
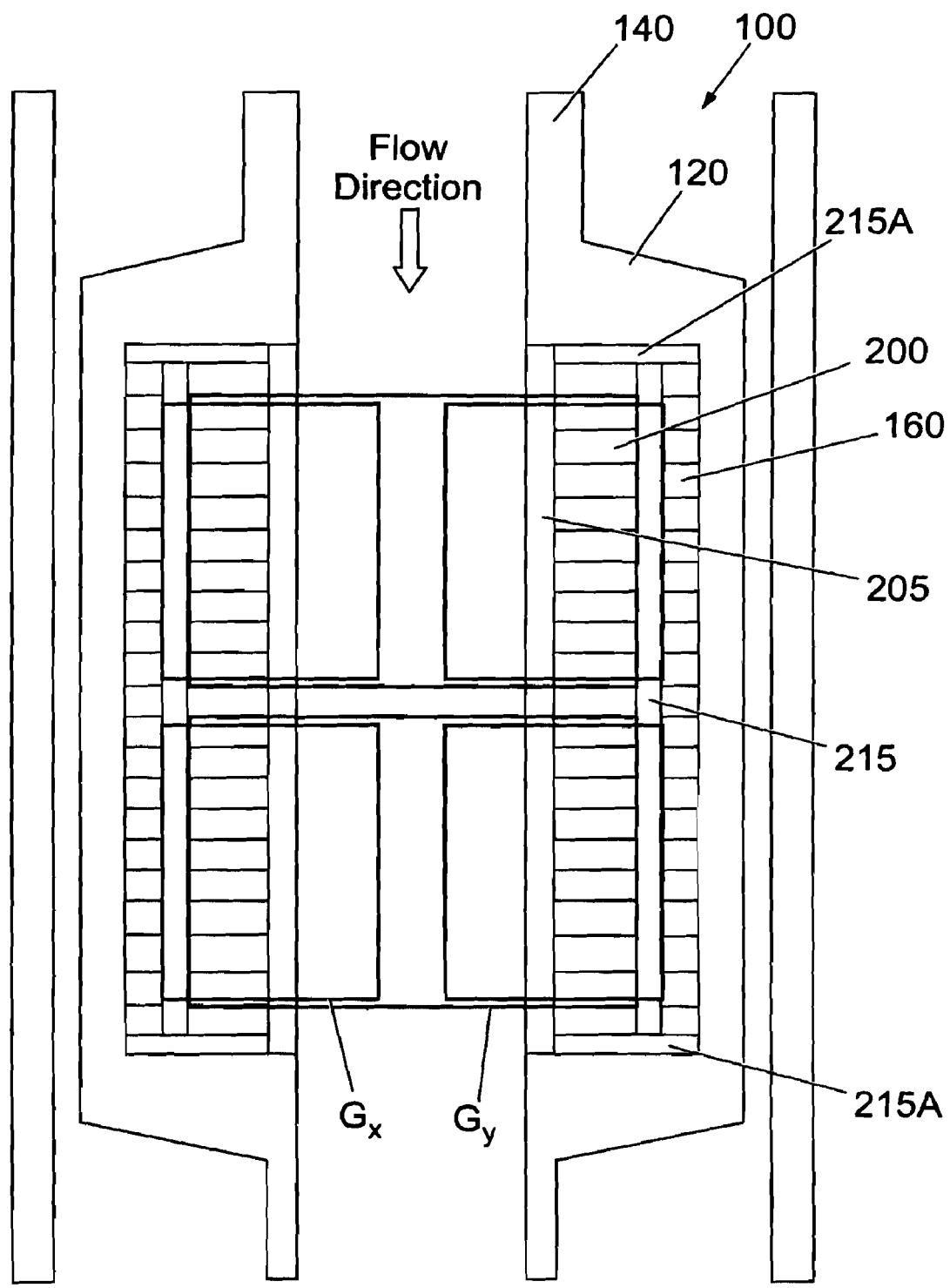
FIG. 13 is a schematic view of the component of the gradient coils of FIG. 10 which act in the x and y-axis directions.

As seen in FIG. 12, tubing 215 houses the axial gradient coil along the flow path (Gz) on the inner surface and the orthogonal gradients (Gx and Gy) on the outer surface (see FIG. 13). Again, these coils are provided in recessed tracks on the tubing 215 and are insulated from the tubing itself using adhesive insulant. The gradient coils are capable of imparting a variable magnetic field as discussed subsequently and in this regard can be considered as an electromagnet.

The tubing 215 is provided with a tubular inner diameter in order to provide minimal frictional losses to the fluid passing therethrough, and a dodecagonal outer surface which allows the tubing to fit within the rings of magnets.

In use, each embodiment of the apparatus 10 operates in an identical fashion by utilizing Nuclear Magnetic Resonance (NMR) techniques in order to determine the volume fraction of multiphase flow produced from a wellbore. In addition to determining the fraction of each phase present in the flow, the invention may also be used to determine the rate of fluid flowing from the wellbore. The embodiments described determine the phase fraction of fluid containing oil, gas and water phases; however, it will be understood by the skilled reader that further and/or different phases may be determined using the apparatus and method described.

For clarity the phase fraction analysis process will firstly be described followed by a description of the flow measurement process; however, both of these processes may be effectively carried out simultaneously by configuring the control system of the apparatus 10 to rapidly alternate between fraction analysis mode and flow measurement mode. This alternation between modes is typically performed at a rate of approximately one second for each mode i.e. the control system will allow the fraction analysis mode to operate for one second and then allow the flow measurement mode to operate for one second before switching back to the fraction analysis mode and so on as required. The skilled reader will note that this time may be altered to suit the specific situation.

The method of using the first embodiment of the apparatus will be described in the following description; however, the skilled reader will realize that either embodiment may be used.

In the embodiment shown, the apparatus 10 is installed in-line with a fluid flow pipe 14. As produced fluids flow into the apparatus 10, they enter the substantially homogeneous primary magnetic field generated by primary magnet 16. Atomic nuclei having a non-zero magnetic moment that are present in the fluids flowing through the apparatus 10 align themselves with the axis of the primary magnetic field. Fluids having a non-zero magnetic moment include $^1$H, $^{13}$C, $^{31}$P and $^{15}$N. In this embodiment (and in many NMR applications in general) $^1$H is the most commonly measured of these since it is naturally present in hydrocarbons such as those produced from wellbores. The nuclei of flow within the throughbore 36 of the apparatus 10 including water, oil and gas are now aligned with the direction of the primary magnetic field.

A radio frequency (RF) pulse signal is now transmitted into the throughbore 36 using the transmission circuit 48 of the combined transmission and reception coils 24. The frequency of the RF pulse will be transmitted at a frequency which is known to excite the atomic nucleus of $^1$H (typically in the region of between 40-45 MHz for a 1 Tesla static magnetic field such that it resonates at its natural resonant frequency (this is known as the Larmour frequency). This ensures that any $^1$H nuclei present in fluid flowing through the throughbore 26 will resonate in response to the RF pulse signal. The frequency (v) required to resonate the nuclei may be determined using the following equation:

$$v = \frac{\gamma B}{2\pi} \qquad \text{Eq. (1)}$$

where $\gamma$ is the gyromagnetic ratio of the nucleus and B is the magnetic field.

While resonating, the nuclei emits a radio signal at a frequency corresponding to its resonating frequency.

The frequency at which the nuclei present in the fluid flow resonate after having being excited by the RF pulse signal is detected by the receiver circuit 40 of the combined transmitter and reception coils 24. In a mixture of phases such as in the present embodiment, the resonance described provides molecular information such as the bond type and the environment surrounding the nuclei. From this, the ratio of the signal being received from the resonating nuclei to the background frequency of the RF pulse may be calculated. The skilled reader will understand that this value is known as Chemical Shift and is measured in parts per million ("ppm").

The chemical shift ($\delta$) recorded by the apparatus may now be used to determine the ratio of oil and gas (combined) to water using the following equation:

$$\delta = \frac{v_{sample} - v_{reference}}{v_{reference}} \times 10^6 \text{ ppm} \qquad \text{Eq. (2)}$$

In this regard, the separation between the phases is increased by ensuring that good magnetic field homogeneity is provided by the primary permanent magnet 16 in order to produce a relaxation time graph peak with a small bandwidth.

However, as stated previously it is desirable to measure the ratio of oil to gas also in order to determine the ratios of oil, gas and water in the multiphase fluid, without assuming presence of other phases. In general, the chemical shift between oil and gas nuclei is too small to measure accurately by using the chemical shift method. Therefore, the present invention determines the ratio of oil to gas by comparing the $T_1$ relaxation times (described subsequently) of each hydrocarbon. This is possible since the $T_1$ relaxation times of gaseous hydrocarbons are longer compared to the $T_1$ relaxation times of liquid hydrocarbons.

In addition to causing the nuclei of each phase to resonate, the energy supplied by the RF pulse signal from the combined transmission and reception coil 24 causes the nuclei of each phase to be knocked off their previous alignment with the primary magnetic field. After the RF signal has been pulsed, the spins (nuclei which have been subjected to a magnetic field) will tend to relax back to their state of equilibrium in which they are re-aligned along the primary magnetic field. The time taken for the spins to relax back to their state of equilibrium after the RF signal has been pulsed off is known as the $T_1$ relaxation time of the nuclei.

It is possible to measure the $T_1$ relaxation times of the oil and gas using the apparatus 10 by monitoring the angle through which the nuclei of each phase of the flow is tilted with respect to the primary magnetic field at any given time (which must be less than the relaxation time) after the RF signal has been pulsed. This is done by measuring the time taken for the magnitude of the radio frequency received from the nuclei to reach a maximum value in the direction of the primary magnetic field and the time taken for a minimum value in the direction orthogonal to the primary magnetic field direction, which may be performed using the combined transmission and reception coils 24. This results in two distinct $T_1$ relaxation times being detectable; one for the oil phase and one for the gas phase. The proton density (PD) of each hydrocarbon phase is now calculated by integrating the area under each peak of the accumulated $T_1$ relaxation time density. The graph is derived by applying an inverse algorithm to the $T_1$ relaxation time measurement extracted using an inversion recovery sequence. Using the proton density measurement the volume fraction is now calculated using the following equation:

$$V = \frac{MW_s}{\rho_s} \times \frac{1}{Av} \times \frac{PD}{\alpha R_{1H}} \qquad \text{Eq. (3)}$$

where $MW_s$ is the molecular weight, $\rho_s$ is the density of the sample, Av is the Avogadro number, PD is the proton density, $\alpha$ is the natural abundance of $^1H$ and $R_1H$ is the number of $^1H$ for 1 molecule of the phase.

The sequence applied here is such that the required measurement time is less than the transit time ($\tau$) of the flow. The method of determining the proton density is performed using a 1-dimensional hydrogen nuclei (1D-1H) sequence in combination with an inversion recovery sequence for $T_1$ measurement and Carr-Purcell-Meiboom-Gill (CPMG) sequence for $T_2$ measurement.

However, the above merely returns values for the volume of the relevant phases and, as previously mentioned, not the phase fraction. In order to calculate the phase fraction, the following equation may be used:

$$\frac{V_1}{\sum_{I=1}^{N} V_i} = \frac{\frac{MW_1}{\rho_1} \times \frac{PD_1}{R_{1H1}}}{\sum_{i=1}^{n} \left(\frac{MW_i}{\rho_i} \cdot \frac{PD}{R_{1Hi}}\right)} \qquad \text{Eq. (4)}$$

where n is the number of phases present in the sample.

It should be noted that in a sample containing just two phases (a and b), the equation can be simplified to:

$$\frac{V_a}{V_a + V_b} = \frac{1}{1 + \frac{MW_b \times \rho_a + PD_b \times R_{1Ha}}{MW_a \times \rho_b \times PD_a \times R_{1Hb}}} \qquad \text{Eq. (5)}$$

Each of the fractions of oil, gas, and water have therefore been calculated using the apparatus 10 without (as in some previous systems) requiring to assume that once the ratios of two phases in the flow have been calculated the third makes up the rest of the fluid.

The method and apparatus for determining the flow rate of the fluid flow will now be described.

Now that the ratio of each phase has been calculated, the $T_1$ relaxation time of each phase is known. The embodiment shown is capable of employing two alternative methods of calculating the flow rate of each phase through the apparatus 10. The first method is based upon the Time of Flight (TOF) of the spins along the apparatus 10. In this method a pulse signal is applied in a 'slice' at a first location along the throughbore 36 of the apparatus 10 in order to tilt the nuclei at that location. A detection area is then monitored downstream from the location at which the pulse signal was applied. The resultant NMR signal received by the reception circuit 40 of the combined transmission and detection coils 24 will now be increased by every fully tilted spin entering the detection area and will be decreased with every fully tilted spin leaving the detection area. The overall net signal can therefore be related back to the flow of phase through the apparatus. This allows the velocity of the flow (v) to be calculated using the transit time ($\tau$) and the distance of the detection area (d) using the following equation:

$$\tau = \frac{d}{v} \qquad \text{Eq. (7)}$$

The second alternative method of measuring the flow through the apparatus 10 uses the gradiated magnetic field provided by the secondary electromagnet 20. A gradient echo sequence is imparted on the flow such that the nuclei of the flow rotate about their axes. In a stationary flow this results in no net accumulation of phase signals since the nuclei experience the same balanced gradient with respect to time. However, in a dynamic flow the magnetic field experienced by the nuclei will change as the nuclei flow along the throughbore 36 of the apparatus 10 due to the magnetic field gradient provided by electromagnet 20. This variation of magnetic field, dependent upon the movement of the flow along the throughbore 36 of the apparatus 10, results in an accumulation of phase signal. This is dependent upon the velocity of the flow through the apparatus 10 and the strength and duration of the magnetic filed gradient supplied by the electromagnet 20. The accumulation in phase (φ) which may be directly correlated to the velocity of the flow is given by:

$$\phi = \gamma B_0 \int dt + \gamma \int n(t) G_n(t) dt \qquad \text{Eq. (8)}$$

where $B_0$ is the magnetic field provided by the primary magnet, n represents the position of the spins within the throughbore in either the x, y, or z axes (as shown in FIG. 1) and $G_n$ is the magnitude of the magnetic field gradient being applied by the electromagnetic 20 in the n-axis direction.

The method described previously allows both the flow rate and proportion of each phase to be calculated using a single apparatus 10. Furthermore, the system and apparatus described does not require users of the apparatus to be safeguarded from levels of operational danger other than that normally expected in such oil and gas exploration operations. Specifically, the apparatus and method described does not require the user to be protected against e.g. radiation and biological hazards.

Figure 14:
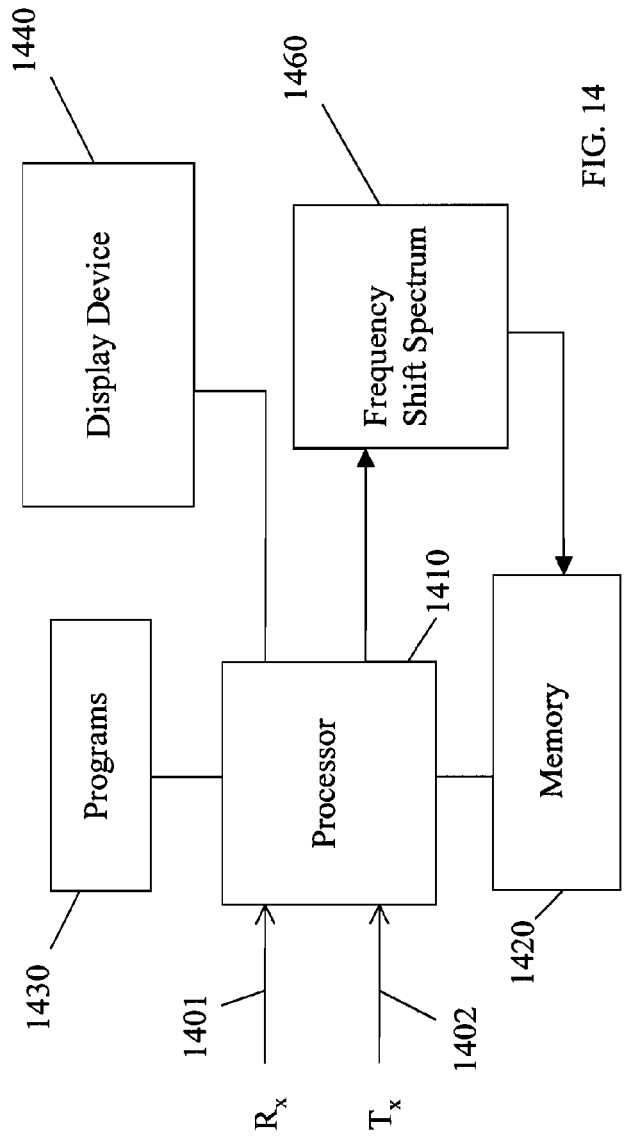
FIG. 14 is a functional diagram of a circuit for performing compositional analysis of hydrocarbons according to one embodiment of the disclosure.

In other aspects, compositional analysis of hydrocarbons produced from the wellbores may be provided using the imparted and detected radio frequency signals. FIG. 14 shows one embodiment of an apparatus that may be utilized for estimating species of hydrocarbons of downhole fluids. The apparatus of FIG. 14, in one aspect, may include a processor, such as a microprocessor or a computer 1410 and a data storage device 1420, which may be any suitable device, including, but not limited to, a solid state memory, compact disc, hard disc, and tape. One or more programs, models and other data (collectively referred to as "programs" and designated by numeral 1430) may be stored in the data storage device 1420 or another suitable device accessible to the processor 1410 for executing instructions contained in such programs. A display device 1440 may be provided for the processor 1410 to display information relating to the compositional analysis, as described in more detail below.

In one aspect, the processor 1410 may compute the frequency difference or frequency shift 1460 between the original imparted or perturbing signal 1402 and the detected signal 1401. This phenomenon is also known as the chemical shift. In one aspect, the processor 1410 may estimate or determine the composition (species of the produced hydrocarbons) using the frequency or chemical shift.

Figure 15:
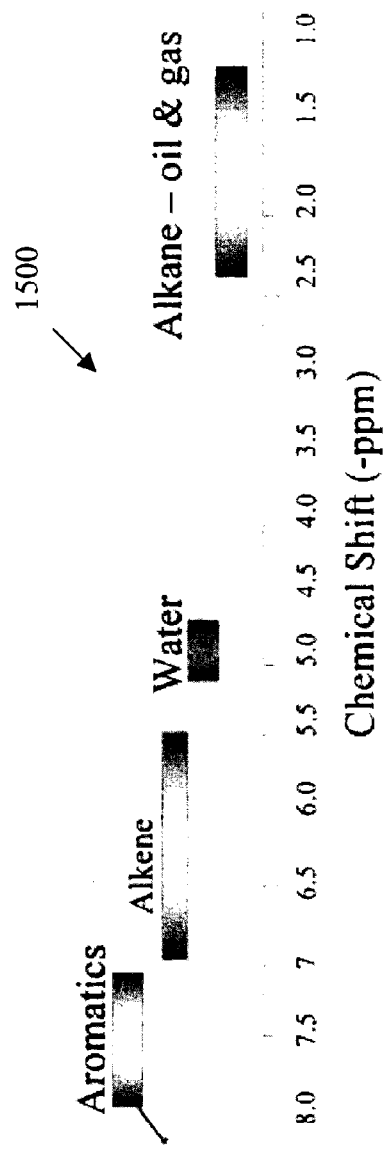
FIG. 15 is a visual representation of the relationship between certain species of a hydrocarbon and the frequency shift (also referred to as chemical shift) between an imparted radio frequency signal on a fluid and a detected radiofrequency signal from the fluid.

FIG. 15 shows a relationship 1500 of the frequency or chemical shift and various species of a hydrocarbon. For example, a chemical shift between −2 to −1.0 parts per million (ppm) indicates the presence of alkane, a chemical shift between −7 to −5.5 ppm indicates the presence of Alkene, and a chemical shift between −8.0 and −7.0 ppm indicates the presence of aromatic compounds. Aromatic compounds are the compounds that have a benzene ring structure, such as toluene, benzene and zylene. The data shown in FIG. 15 may be stored in the data storage device 1420 for use by the processor 1410.

Figure 16:
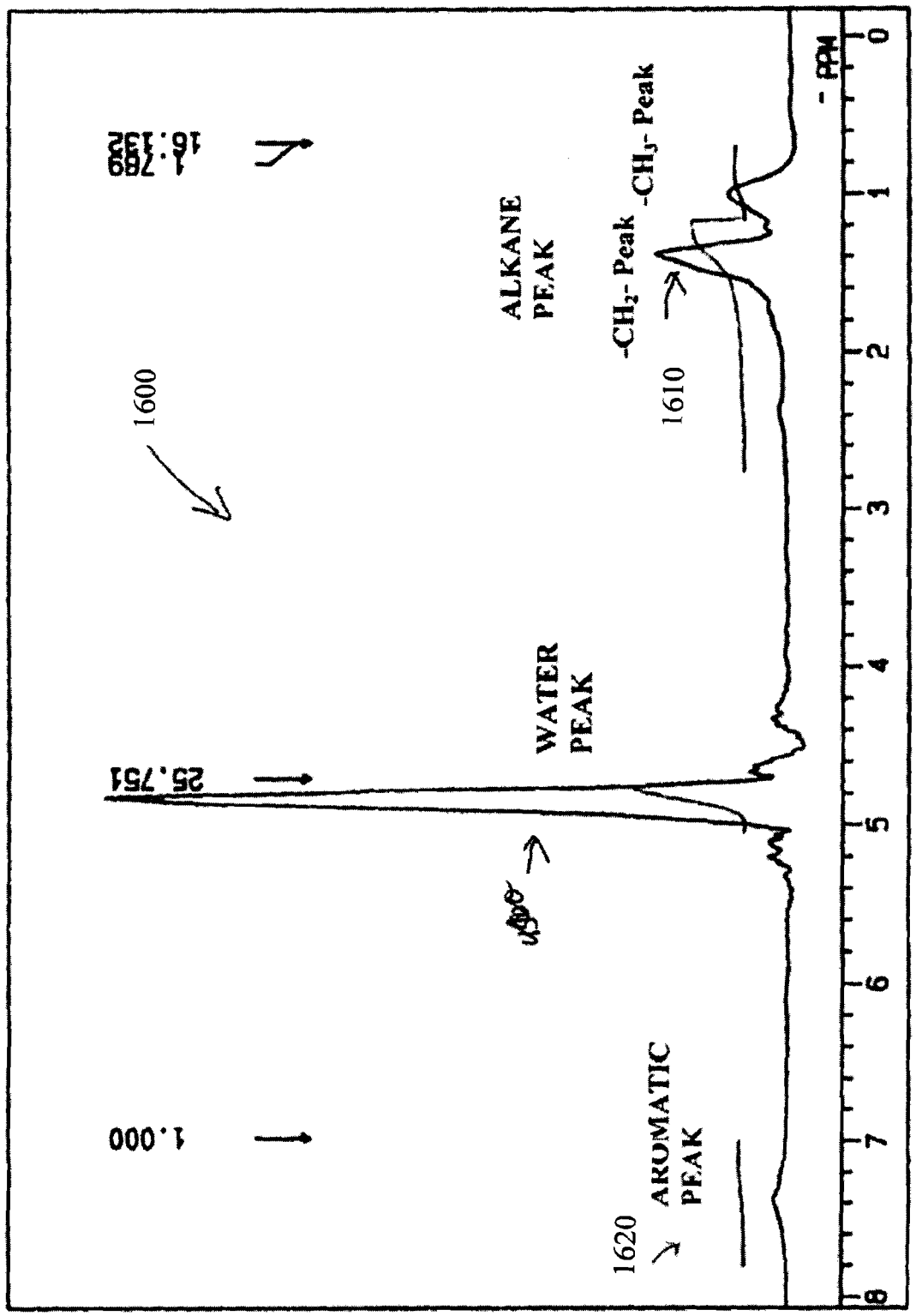
FIG. 16 is a frequency shift spectrum of certain species of a hydrocarbon.

FIG. 16 shows a chemical shift curve or spectrum 1600 relating to the various species of a hydrocarbon produced from the wellbores. In another aspect, the processor 1410 may estimate an amount of the species from the spectrum 1600. In one aspect, an area under the chemical shift curve 1600 may be integrated to estimate the amount of the species in the hydrocarbon. Therefore, the area under the curve section 1610 will provide the amount or fraction of alkane in the fluid sample, while the area under section 1620 will provide the amount or fraction of aromatics in the fluid sample. Composition of the species may therefore be estimated as a relative value or as an absolute value.

In another aspect, the programs 1430 may include instructions for the processor to determine the relaxation times and provide therefrom a detailed analysis of the species, such as a breakdown of the types of alkanes. Relaxation time, as described previously, is the time the signal emitted by the nuclei takes to decay. There is a direct relationship between the density of the alkane (which is linked to the length of the carbon chain) and the relaxation time. The higher the density of alkane, the longer the relaxation time.

In another aspect, the compositional analysis of hydrocarbon described herein may be utilized to provide information for a PVT analysis of the hydrocarbon. From the estimated composition of the hydrocarbon, as described above, the overall PVT properties of the hydrocarbon may be determined.

In prior art techniques, the PVT analysis of the hydrocarbon is typically done by taking a sample of the downhole fluid at a known pressure and temperature and various tests are conducted to determine the properties of the fluid, such as the bubble point and density and viscosity at various temperatures and pressures. The breakdown of the hydrocarbon to its core components is then made. The PVT properties of the core components are well known and may be reconstituted to provide an overall hydrocarbon PVT property. A known reconstitution technique is used. For example, for gas hydrocarbons, gas chromatography may be performed to break down the gas into its individual components and based on this composition, an overall gas property may be recalculated.

The technique of compositional analysis described herein bypasses taking a fluid sample and rigorous tests typically performed to determine the PVT properties of the hydrocarbon. Furthermore, in the present method, the measurements are done in real time (in-situ) as opposed to 'sampling' of the hydrocarbon.

Thus, in view of the above, a method for estimating composition of a hydrocarbon in a fluid flowing downhole may include: imparting a magnetic field on the fluid to align nuclei of the fluid with a direction of the primary magnetic field; imparting a perturbing or first radio frequency signal on the fluid to excite the nuclei of the fluid; detecting a second radio frequency signal emitted by the excited nuclei of the fluid; estimating a frequency shift between the perturbing radio frequency and the detected radio frequency; and estimating using the frequency shift a composition of the hydrocarbon. The composition may relate to one or more species that are selected from a group consisting of: (i) alkane; (ii) alkene; and (iii) an aromatic compound. The aromatic compound may comprise: toluene, benzene and zylene. In another aspect, the method may estimate an amount of a species in the hydrocarbon by: preparing a frequency shift curve; integrating an area under the frequency shift curve corresponding to at least one species; and estimating an amount of the at least one species from the integrated area. In another aspect, a method according to the disclosure may further estimate a density of a species by: estimating a relaxation time of the nuclei from the detected radio frequency signal; and estimating the density of the species from the relaxation time. Yet, in another aspect, a method according to one aspect of the disclosure may further perform a PVT analysis utilizing the estimated properties of the species.

In another aspect, an apparatus may include: a magnet configured to induce a magnetic field in a region of the downhole fluid; a transmitter configured to impart a radio frequency signal in the region of the downhole fluid; a receiver configured to receive a radio frequency signal from the fluid;

and a processor configured to estimate a composition of the hydrocarbon in the downhole fluid. In another aspect, the processor may be configured to: prepare a frequency shift curve; integrate an area under the frequency shift curve corresponding to the species; and estimate a quantity of the species in the fluid from the integrated area. In another aspect, the processor may further be configured to: estimate a relaxation time of the nuclei from the detected signal; and estimate density of a species from the relaxation time. In another aspect, the processor may be configured to perform a PVT analysis utilizing the estimated properties of the species. In yet another aspect, the magnet may further comprise an outer magnet layer that provides a substantially homogenous magnetic field and an inner layer spaced apart from the outer magnet by a spacer. Further, in one aspect, the magnet may be provided with end members that span across the spacer. The spacer may include a tubular member located between the outer and inner layers. Further, a common coil may be used as a transmitter and a receiver.

The dimensions of the apparatus may be altered during the manufacturing stage dependent upon the particular downhole or subsea conditions in which it is to be used. In this regard, the space requirements of the components may be balanced based on the accuracy of desired measurement, which may be relevant for the primary magnet 16 and the electromagnet 20. Additionally, the apparatus described above may be used in a wellbore or in-line with any portion of the production tubing. Alternatively the apparatus may be used off site as an off-site measurement and analysis tool.

While the foregoing disclosure is directed to certain embodiments, various modifications will be apparent to those skilled in the art. It is intended that all such modifications fall within the scope and spirit of this disclosure and any claims that are or may be presented.

What is claimed is:

1. A method of estimating a composition of a fluid flowing downhole, comprising:
    imparting a substantially homogeneous magnetic field on the fluid to align nuclei of the fluid with a direction of the primary magnetic field of a permanent magnet;
    imparting a perturbing radio frequency signal on the fluid to excite the nuclei of the fluid from a transmitter;
    detecting a radio frequency signal emitted by the excited nuclei of the fluid at a receiver; and
    using a processor to:
    estimate a frequency shift between the perturbing radio frequency signal and the detected radio frequency signal, and
    use the frequency shift to estimate an amount of one or more hydrocarbon species in the fluid to estimate the fluid composition.

2. The method of claim 1, wherein the one or more hydrocarbon species are selected from a group consisting of: (i) alkane; (ii) alkene; and (iii) an aromatic compound.

3. The method of claim 1, wherein the one or more hydrocarbon species are selected from a group consisting of: toluene, benzene and zylene.

4. The method of claim 1 further comprising using the processor to:
    prepare a frequency shift curve;
    integrate an area under the frequency shift curve corresponding to at least one hydrocarbon species; and
    estimating the amount of the at least one hydrocarbon species from the integrated area.

5. The method of claim 1 further comprising using the processor to:
    estimate a relaxation time of the nuclei from the detected radio frequency signal; and
    estimate a density of the one or more hydrocarbon species from the relaxation time.

6. The method of claim 1 further comprising performing a PVT analysis utilizing the estimated composition of the one or more hydrocarbon species.

7. An apparatus for estimating a composition of a downhole fluid, comprising:
    a magnet configured to impart a substantially homogeneous magnetic field in a region of the downhole fluid;
    a transmitter configured to impart a radio frequency signal in the region of the downhole fluid;
    a receiver configured to receive a radio frequency signal from the fluid; and
    a processor configured to:
    estimate a frequency shift between the imparted radio frequency signal and the received radio frequency signal, and
    use the frequency shift to estimate an amount of one or more hydrocarbon species in the downhole fluid to estimate the composition of the downhole fluid.

8. The apparatus of claim 7, wherein the processor is further configured to:
    prepare a frequency shift curve;
    integrate an area under the frequency shift curve corresponding to at least one hydrocarbon species; and
    estimate the amount of the at least one hydrocarbon species in the fluid from the integrated area.

9. The apparatus of claim 7, wherein the one or more hydrocarbon species is one of: (i) alkane; (ii) alkene; and (iii) an aromatic compound.

10. The method of claim 9, wherein the one or more hydrocarbon species is an aromatic compound that include at least one of: toluene, benzene and zylene.

11. The apparatus of claim 7, wherein the processor is further configured to:
    estimate a relaxation time of the nuclei from the detected signal; and
    estimate density of the one or more hydrocarbon species from the relaxation time.

12. The method of claim 7 further comprising performing a PVT analysis utilizing the estimated composition of the one or more hydrocarbon species.

13. The apparatus of claim 7, wherein the magnet comprises an outer magnet layer that provides the substantially homogenous magnetic field.

14. The apparatus of claim 8, wherein the magnet further comprises an inner layer spaced apart from the outer magnet layer by a spacer.

15. The apparatus of claim 14, wherein the magnet is provided with end members that span across the spacer.

16. The apparatus of claim 14, wherein the spacer comprises a tubular member located between the outer and inner layers.

17. The apparatus of claim 7, wherein the transmitter and receiver constitute a combined transmission and reception coil.

18. The apparatus according to claim 17, wherein the combined transmission and reception coil is provided in a coil housing located on an inner bore of the apparatus.

* * * * *

UNITED STATES PATENT AND TRADEMARK OFFICE
CERTIFICATE OF CORRECTION

PATENT NO. : 8,248,067 B2  
APPLICATION NO. : 12/348068  
DATED : August 21, 2012  
INVENTOR(S) : Joo Tim Ong Page 1 of 1

It is certified that error appears in the above-identified patent and that said Letters Patent is hereby corrected as shown below:

Line (63) under "Related U.S. Application Data", first sheet of issued patent reads:

"Continuation-in-part of application No. 11/233,900, filed on Sep. 23, 2005, now Pat. No. 7,501,819."

Line (63) under "Related U.S. Application Data", first sheet of issued patent should read:

--Continuation-in-part of application No. 11/233,900, filed on Sep. 23, 2005, now Pat. No. 7,501,819, which claims priority from United Kingdom Patent Application No. 0421266.8, filed on Sep. 24, 2004, all of which are hereby incorporated by reference in their entirety.--

Signed and Sealed this  
Thirteenth Day of November, 2012

David J. Kappos  
*Director of the United States Patent and Trademark Office*